United States Patent
Ollivier

(10) Patent No.: US 11,484,703 B2
(45) Date of Patent: Nov. 1, 2022

(54) SUBCUTANEOUS LEAD FOR AN IMPLANTABLE CARDIAC DEVICE

(71) Applicant: SORIN CRM SAS, Clamart (FR)

(72) Inventor: Jean-Francois Ollivier, Gif sur Yvette (FR)

(73) Assignee: Sorin CRM SAS, Clamart (FR)

( * ) Notice: Subject to any disclaimer, the term of this patent is extended or adjusted under 35 U.S.C. 154(b) by 190 days.

(21) Appl. No.: 16/920,090

(22) Filed: Jul. 2, 2020

(65) Prior Publication Data

US 2021/0001112 A1   Jan. 7, 2021

(30) Foreign Application Priority Data

Jul. 5, 2019   (FR) ........................................ 1907535

(51) Int. Cl.
    *A61N 1/05*    (2006.01)
    *A61N 1/39*    (2006.01)
    *A61N 1/365*    (2006.01)

(52) U.S. Cl.
CPC ......... *A61N 1/0504* (2013.01); *A61N 1/0597* (2013.01); *A61N 1/365* (2013.01); *A61N 1/3987* (2013.01); *A61N 1/39622* (2017.08)

(58) Field of Classification Search
CPC .......................... A61N 1/0504; A61N 1/39622
USPC .......................................................... 607/7
See application file for complete search history.

(56) References Cited

U.S. PATENT DOCUMENTS

| | | | | |
|---|---|---|---|---|
| 6,104,961 | A * | 8/2000 | Conger | A61N 1/056 607/122 |
| 6,192,280 | B1 * | 2/2001 | Sommer | A61N 1/0565 607/122 |
| 8,437,864 | B2 * | 5/2013 | Seifert | A61N 1/0563 607/116 |
| 9,724,126 | B2 * | 8/2017 | Gerber | A61N 1/0558 |
| 2007/0156219 | A1 * | 7/2007 | Sommer | A61N 1/0573 607/131 |
| 2013/0184550 | A1 * | 7/2013 | Forslund | A61B 5/055 29/605 |
| 2014/0005513 | A1 | 1/2014 | Osypka | |

FOREIGN PATENT DOCUMENTS

| | | |
|---|---|---|
| JP | 08-080353 A | 3/1996 |
| WO | WO-93/09840 A1 | 5/1993 |
| WO | WO-02/45795 A2 | 6/2002 |

OTHER PUBLICATIONS

European office action on EP Application No. 20183491.8 dated Dec. 1, 2020. 7 pages.
Foreign Search Report for FR Patent Application No. 1907535, dated Apr. 27, 2020. 8 pages.
Office action issued in JP Application No. 2020-115479 dated Sep. 17, 2021.

* cited by examiner

*Primary Examiner* — Nicole F Lavert
(74) *Attorney, Agent, or Firm* — Foley & Lardner LLP

(57) ABSTRACT

A subcutaneous lead for an implantable cardiac device, in particular for a defibrillator or/and a pacemaker comprising a lead body, itself comprising at least one sensing electrode and an insulating sleeve into which the lead body is threaded so that the insulating sleeve and the lead body are movable relative to each other so as to at least partially cover the at least one sensing electrode with the insulating sleeve.

12 Claims, 3 Drawing Sheets

SUBCUTANEOUS LEAD FOR AN IMPLANTABLE CARDIAC DEVICE

CROSS-REFERENCE TO RELATED PATENT APPLICATIONS

This application claims the benefit of and priority to French Application No. 1907535, filed Jul. 5, 2019, which is incorporated herein by reference in its entirety.

BACKGROUND

The present invention relates to a subcutaneous lead for an implantable cardiac device, in particular for a defibrillator or/and a pacemaker.

In the example of an implantable defibrillator, a subcutaneous lead has a double function: it allows, by means of sensing electrodes, to detect an electrical surface activity in order to deduce therefrom the cardiac activity of a patient and, if necessary, to deliver a defibrillation shock.

However, the quality of the detection of an electrical surface activity (therefore distant from the cardiac mass) can be impaired by many artefacts such as electrical muscle surface noise, interference with the external environment etc. In addition, it largely depends on the positioning of the sensing electrodes. Therefore, the practician must find, during the implantation of the subcutaneous lead, a compromise of positioning which is acceptable to ensure the dual function of the lead; sometimes to the detriment, depending on the patient's morphology, of the detection or defibrillation function. This is notably due to the fact that the known subcutaneous leads are of fixed geometry, that is to say that the relative positioning of the electrodes is fixed relative to the lead body and cannot take into account the different morphologies of the patients.

Furthermore, the distance to the excitable muscle and the configuration of the known subcutaneous leads (in particular the inter-electrode distance and the fact of using annular sensing electrodes) are not suitable for creating a sufficiently effective distant electric field on a part of the heart muscle that can allow a pacing function.

SUMMARY

The object of the present invention is thus to propose a subcutaneous lead for an implantable cardiac device which makes it possible to improve the quality of the detection of an electrical surface activity. In addition, the object of the invention is to provide a subcutaneous lead suitable for delivering electrical impulses to the heart muscle.

The object of the present invention is achieved by a subcutaneous lead for an implantable cardiac device, in particular for a defibrillator or/and a pacemaker, comprising a lead body itself comprising at least one sensing electrode; and further comprising an insulating sleeve into which the lead body is threaded so that the insulating sleeve and the lead body are movable relative to each other so as to at least partially cover the electrode of detection by the insulating sleeve.

Thus, by virtue of its movable nature, the insulating sleeve according to the present invention makes it possible to meet the limitations induced by the fixed configuration of the sensing electrode relative to the lead body. Therefore, the insulating sleeve of the present invention allows a practician to have a subcutaneous lead with a sensing electrode with variable geometry, thus making it possible to best adapt to the morphology of a patient. Indeed, the lead body and the insulating sleeve being movable relative to each other, the longitudinal positioning of the insulating sleeve relative to the lead body is adjustable by the practician during the implantation of the lead. The variable geometry subcutaneous lead of the present invention is thus adapted to minimize the detection of surface muscle noise and therefore to avoid the detection of artifacts which can lead to the delivery of inappropriate shock.

The present invention, relating to a subcutaneous lead for an implantable cardiac device, can be further improved by the following embodiments.

According to one embodiment of the invention, the insulating sleeve can have a length along a central axis of the insulating sleeve longer than a length of the sensing electrode along a central axis of the sensing electrode; and the insulating sleeve can comprise a side opening in a side wall of the insulating sleeve so that the side opening can be positioned above the sensing electrode.

The lateral opening of the insulating sleeve makes it possible to selectively expose at least partially a surface of the sensing electrode. The positioning of the insulating sleeve relative to the sensing electrode and to the lead body thus makes it possible to adjust both the positioning of the sensing electrode relative to the lead body, but also the exposed surface of the sensing electrode. Thus, thanks to the insulating sleeve making the parameters of positioning and exposure surface of the sensing electrode adjustable, the subcutaneous lead of the present invention makes it possible to refine the positioning of the sensing electrode and to improve the detection of the cardiac activity of a patient.

According to one embodiment of the invention, the insulating sleeve, respectively the lead body, can be movable longitudinally and/or radially relative to a central axis of the lead body, respectively to a central axis of the insulating sleeve.

Therefore, the insulating sleeve of the present invention also allows, in addition to the positioning and exposure surface parameters of the adjustable sensing electrode, to selectively adapt the orientation of the exposed surface of the sensing electrode, that is to say the orientation of the surface of the sensing electrode, which is below the lateral opening of the insulating sleeve. Thus, the quality of the detection of the electrical surface signals can be further improved by this additional adjustment parameter constituted by the active (exposed) surface orientation of the sensing electrode. Furthermore, the orientation of the exposed surface of the sensing electrode also makes it possible, in the case of a lead for a cardiac stimulation device, to orient an electric field towards the patient's cardiac mass.

According to an embodiment of the invention, the lead body can also comprise a second sensing electrode; the insulating sleeve can at least partially cover the first sensing electrode and the second sensing electrode.

Thus, in the case of a subcutaneous lead comprising two sensing electrodes, the insulating sleeve also allows a practician to vary the respective exposed surface of the two sensing electrodes. By positioning the insulating sleeve with respect to the first and second sensing electrodes in a manner suited to the morphology of a patient, the quality of the detection of surface electrical signals by the two sensing electrodes can thus be improved.

According to one embodiment of the invention, the insulating sleeve can comprise two lateral openings in a side wall of the insulating sleeve so that a first lateral opening can be positioned above the first sensing electrode and a second lateral opening can be positioned above the second sensing electrode.

It is then possible to preferentially define, during the design of the insulating sleeve, the distance between the two lateral openings and thus to control the distance between the respective exposed surfaces of the sensing electrodes, which form a dipole. In addition, it is possible to move along the lead body the position of the dipole formed by the two sensing electrodes by means of the insulating sleeve and, thus, to adjust its positioning as well as possible (relative to two opposite ends of the lead body lead) depending on the quality of detection of electrical surface signals.

According to an embodiment of the invention, the lead can further comprise a third sensing electrode disposed distally on the lead body; and a defibrillation electrode; such that the defibrillation electrode can be positioned between the third sensing electrode and an assembly formed by the first electrode and the second sensing electrode; the insulating sleeve at least partially covering the first and the second sensing electrodes.

The subcutaneous lead according to the present invention is thus configured for a defibrillator. The insulating sleeve geometrically dissociates the detection function (of the sensing electrodes) from the defibrillation function (of the defibrillation electrode). Indeed, the movement of the insulating sleeve on the lead body makes it possible to prevent the optimization of the detection of the surface electrical signals by the first and the second sensing electrodes from being made to the detriment of the position of the defibrillation electrode.

According to an embodiment of the invention, the assembly formed by the first and second sensing electrodes can be configured for a cardiac stimulation function.

Thus, the subcutaneous lead of the present invention is also adapted for a cardiac stimulation device so that the assembly formed by the first and second sensing electrodes is capable of creating an electric field and that this electric field is oriented towards a patient's heart mass by means of the insulating sleeve.

According to one embodiment of the invention, a first portion of the insulating sleeve along a central axis of the insulating sleeve can comprise a side wall which itself comprises at least one flat surface, in particular a portion of the insulating sleeve along a central axis of the insulating sleeve can have a cross section with respect to a central axis of the insulating sleeve of essentially polygonal geometry, preferably triangular.

The flat surface of the side wall of the insulating sleeve provides a support surface for the insulating sleeve with the muscle tissue of a patient. The flat surface then makes it possible to maintain, in particular by friction, the orientation of the insulating sleeve relative to the lead body once implanted in the body of a patient, avoiding an involuntary rotational movement of the insulating sleeve around the lead body, during implantation or during the life of the implanted patient.

The essentially polygon geometry, preferably triangular, of a portion of the insulating sleeve makes it possible to further improve the maintenance of the orientation of the insulating sleeve relative to the lead body in the body of a patient, by offering more support between said portion of the insulating sleeve and the muscle tissue of a patient.

According to one embodiment of the invention, a second portion of the insulating sleeve along a central axis of the insulating sleeve can comprise at least one fixing means configured to prevent longitudinal movement of the insulating sleeve relative to a central axis of the lead body and/or for attaching the insulating sleeve to muscle tissue.

The fixing means ensures that the insulating sleeve is kept in its optimal position defined by the practician after the implantation of the subcutaneous lead. The adjusted positioning of the sensing electrode can thus be maintained and ensured during the life of the implanted patient.

According to one embodiment of the invention, the lead body can comprise at least one stop element projecting from the lead body at least partially around the lead body capable of blocking a longitudinal movement of the insulating sleeve relative to a central axis of the lead body.

The stop element of the lead body thus makes it possible to control the amplitude of the longitudinal displacement of the insulating sleeve relative to a central axis of the lead body.

According to one embodiment of the invention, at least one sensing electrode can be a flexible electrode comprising one or more filaments wound(s) around the lead body, in particular at least one electrode from the first sensing electrode and the second sensing electrode of the lead.

The advantage of flexible electrodes is that they make it possible to avoid stiffening the lead body, in comparison with conventional rigid electrodes, in particular long electrodes with silicone under layer, which contributes to avoid weakening the lead over time and/or be uncomfortable for the patient.

The present invention thus makes it possible to avoid the use of conventional lead comprising rigid detection rings.

According to one embodiment of the invention, the insulating sleeve can be made in at least two separate parts, each part of the insulating sleeve comprising at least one lateral opening.

It is thus possible to adapt the design of the subcutaneous lead of the present invention to several sets of insulating sleeve in order to best adjust to the needs of the patient and the practician, in particular by varying the inter-electrode distance. In addition, the at least two separate parts of the insulating sleeve can have side openings of different dimensions. It is also possible to offer different openings specifically adapted to the needs of the patient and the practician.

According to an embodiment of the invention, the insulating sleeve can comprise a radio opaque material.

Thus, the insulating sleeve has the advantage of being detectable and can therefore be identified during a medical radiography.

BRIEF DESCRIPTION OF THE DRAWINGS

The invention and its advantages will be explained in more detail below by means of preferred embodiments and based in particular on the following accompanying figures, in which.

DETAILED DESCRIPTION

The invention will now be described in more detail using advantageous embodiments in an exemplary manner and with reference to the drawings. The embodiments described are simply possible configurations and it should be borne in mind that the individual characteristics as described above can be provided independently of each other or can be omitted altogether during the implementation of the present invention.

Figure 1:
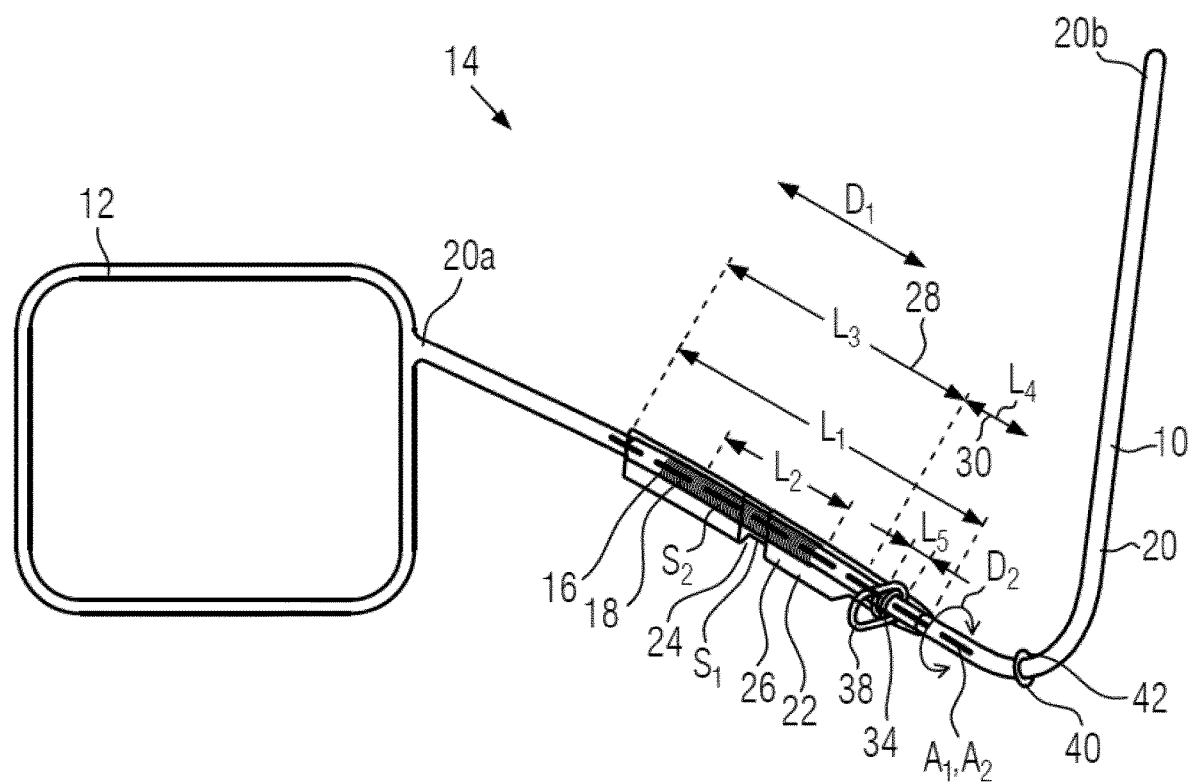
FIG. 1 represents a schematic and transparent view of a subcutaneous lead according to a first embodiment of the present invention.

FIG. 1 illustrates a subcutaneous lead 10, according to a first embodiment, connected to a housing 12 of a medical device 14, which is implanted subcutaneously.

Figure 2:
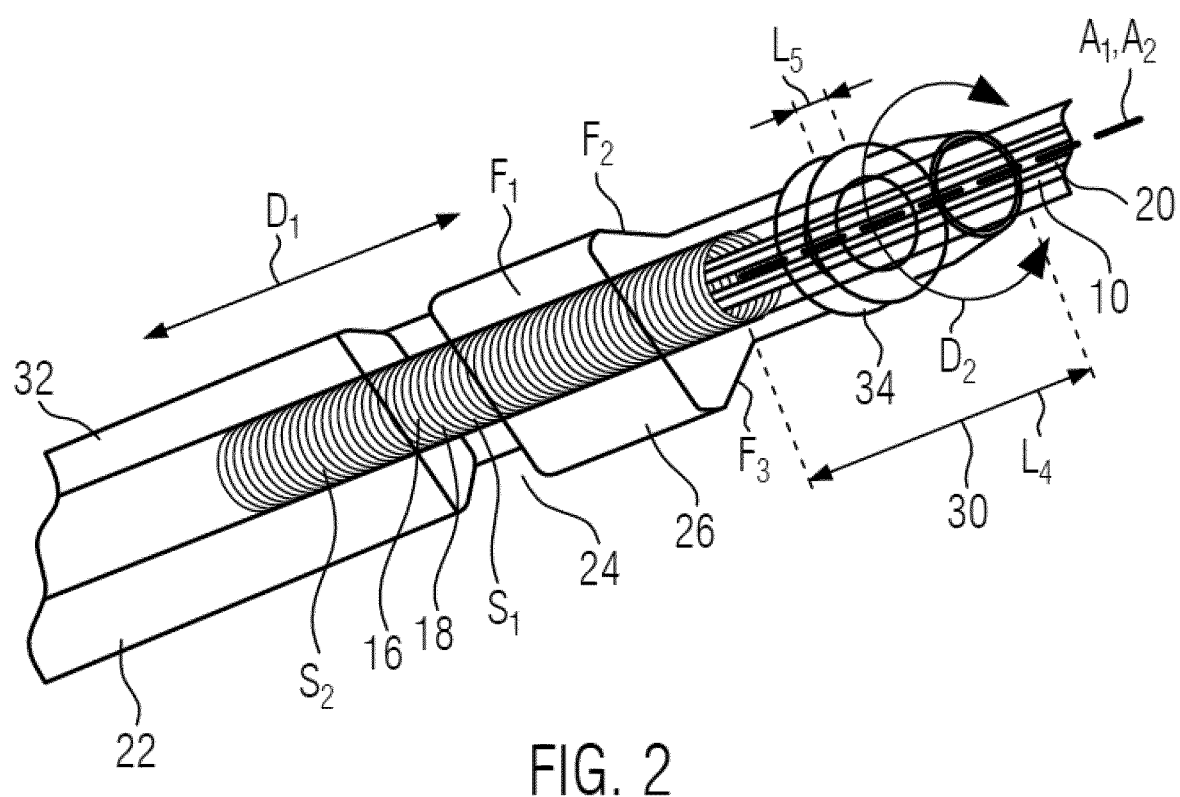
FIG. 2 represents an enlargement of FIG. 1 of the subcutaneous lead according to the first embodiment.

FIG. 2 being an enlargement of a section of the subcutaneous lead 10, FIGS. 1 and 2 will be described jointly in the following.

According to the first embodiment, the lead 10 comprises a sensing electrode 16. In a variant where the medical device 14 is an implantable defibrillator 14, the subcutaneous lead further comprises a defibrillation electrode. Such a device will be further described with reference to FIG. 3.

The sensing electrode 16 is formed of a monofilament 18 wound around the lead body 20, visible on the enlargement of FIG. 2. The sensing electrode 16 is thus a flexible electrode unlike the conventional leads known from the prior art which are provided with rigid detection rings. The sensing electrode 16 can be partially coated with a silicone or polyurethane under layer.

The lead body 20 is delimited by two ends 20a, 20b, one of which (20a) is connected to the housing 12 and the other (20b) corresponds to the distal end of the lead 10, visible in FIG. 1.

The sensing electrode 16 of the subcutaneous lead 10 allows the detection of surface electrical signals whose processing makes it possible to deduce therefrom the cardiac activity of a patient.

The detection of electrical activity on the surface is however altered by many artefacts such as electrical muscle noise from the surface or interference with the outside environment. The quality of the detection thus largely depends on the positioning of the sensing electrode 16 in the patient's body.

In order to control the positioning of the sensing electrode 16 to improve the quality of surface detection, the subcutaneous lead 10 of the present invention comprises an insulating sleeve 22 into which the lead body 20 is threaded. The insulating sleeve 22 can be made of polyurethane in order to give it a certain torsional rigidity. Alternatively, the insulating sleeve 22 can be made of biocompatible silicone (50 or 65 Shore). In another variant, the insulating sleeve 22 further comprises a radio opaque material, such as barium sulfate, in order to make the insulating sleeve 22 detectable during a medical radiography.

The lead body 20 and the insulating sleeve 22 are movable relative to each other so as to at least partially cover the sensing electrode 16 by the insulating sleeve 22. The insulating sleeve 22 is thus movable longitudinally (shown by the double arrow D1) and/or radially (represented by the double arrow D2) relative to a central axis A2 of the lead body 20. Respectively, the lead body 20 can be displaced longitudinally (represented by the double arrow D1) and/or radially (represented by the double arrow D2) relative to a central axis A1 of the insulating sleeve 22.

Thus, the adjustment of the position of the insulating sleeve 22 makes it possible to fulfill the limitations induced by the fixed configuration of the sensing electrode 16 relative to the lead body 20. Therefore, the insulating sleeve 22 allows a practician to have a subcutaneous lead 10 with a sensing electrode 16 with variable geometry, thus making it possible to best adapt to the morphology of a patient and to be able to reduce or even minimize the detection of surface muscle noise (and therefore to avoid the detection of artifacts that could lead to the delivery of inappropriate shock, for example).

The insulating sleeve 22 has a length L1 along a central axis A1 of the insulating sleeve 22 longer than a length L2 of the sensing electrode 16 along a central axis A2 (see FIG. 1). In addition, the insulating sleeve 22 comprises a side opening 24, such as a window, in a side wall 26 of the insulating sleeve 22 so that the side opening 24 is positioned above the sensing electrode 16.

The total area S2 of the sensing electrode 16 is between 200 square millimeters and 500 square millimeters. The insulating sleeve 22 makes it possible to reduce the total area S2 of the sensing electrode 16. The lateral opening 24 of the insulating sleeve 22 thus makes it possible to selectively expose at least partially an area S1 of the sensing electrode 16, that is to say the surface S1 of the sensing electrode 16, which is not covered by the insulating sleeve 22. The area of the exposed surface S1 of the sensing electrode 16 is therefore less than the area of the surface total S2 of the sensing electrode 16. According to the first embodiment, the exposed surface S1 of the sensing electrode 16 has an area of 4 to 30 square millimeters, preferably 10 to 20 square millimeters. The area of the exposed surface S1 can preferably be defined during the design of the insulating sleeve 22 while the positioning of the lateral opening 24 above the sensing electrode 16 is controlled by the practician during the implantation of the subcutaneous lead 10. This gives variable geometry to the subcutaneous lead 10, which makes it possible to improve the quality of the detection on the surface by means of an adjusted positioning of the sensing electrode 16. Thus the distance from the exposed part with respect to the ends 20a, 20b can be adjusted by the practician.

Alternatively, a side wall 26 of the insulating sleeve 22 may be provided with at least two side openings. In addition, the geometry of the lateral opening 24 can vary from one insulating sleeve 22 to another, and can, in particular, be specifically designed to adapt to the specific needs of detection or/and stimulation of a patient. The specific shape of the lateral opening 24 of the insulating sleeve 22 according to the first embodiment illustrated in FIGS. 1 and 2 is therefore not limiting and could be designed with a different geometry—at least as long as the lateral opening 24 allows exposing an area S1 of the sensing electrode 16 which is less than the total area S2 of the sensing electrode 16.

The lateral opening 24 of the insulating sleeve 22 makes it possible to obtain a sensing electrode 16 of sectoral type and not annular. The sectoral nature of the lateral opening 24 of the insulating sleeve 22 makes it possible in particular to preferentially orient the exposed surface of the sensing electrode towards the cardiac mass. The preferential orientation of the exposed surface S1 of the sensing electrode 16, in particular towards the muscle mass of the implanted patient, makes it possible in particular to minimize the detection of surface muscle noise and therefore potentially to avoid the detection of artifacts which may lead to inappropriate shock.

According to the first embodiment, the insulating sleeve 22 is formed in one piece which comprises along a central axis A1 a first portion 28 of length L3 and a second portion 30 of length L4. According to the first embodiment, the first portion 28 of the insulating sleeve 22 has a substantially polygonal cross section, here triangular, while the second portion 30 of the insulating sleeve 22 has a substantially circular cross section.

The first portion 28 of the insulating sleeve 22 is thus provided with a side wall 32 along a central axis A1 of the insulating sleeve 22 which essentially comprises three flat faces F1, F2, F3 (see FIG. 2).

In a variant, the first portion 28 of the insulating sleeve 22 does not necessarily have a triangular geometry section but comprises a side wall along a central axis A1 of the insulating sleeve 22 itself comprising at least one flat surface.

The flat faces F1, F2, F3 of the side wall 32 of the first portion 28 of the insulating sleeve 22 each provide a support surface for the insulating sleeve 22 with muscle tissue of a patient. The flat faces F1, F2, F3 then make it possible to maintain, in particular by friction, the orientation of the insulating sleeve 22 relative to the lead body 20 in the body of a patient, by avoiding an involuntary movement in rotation (represented by the double arrow D2) of the insulating sleeve 22 around the lead body 20, during implantation and during the life of the implanted patient.

The second portion 30 of the insulating sleeve 22, the cross section of which is essentially circular, comprises, for its part, a fixing means 34 allowing a practician to immobilize the insulating sleeve 22 relative to the lead body 20, and to attach the insulating sleeve 22 and lead body 20 assembly to the muscle tissue of a patient.

According to the first embodiment of the invention, the fixing means 34 is provided by a groove 36 on the second portion 30 which is transverse to a central axis A1 of the insulating sleeve 22. The groove 36 has a width L5 adapted to receive a ligature wire 38. Thus, once the positioning defined by the practician, depending on the quality of the electrical signals detected for example, the insulating sleeve 22 and the lead body 20 are then secured at the level of a patient's chest by a conventional ligation technique, the ligation wire 38 encompassing both the insulating sleeve 22 and the lead body 20 at the groove 36, and the patient's muscle tissue.

FIG. 1 further illustrates a stop element 40 disposed on the lead body 20 which makes it possible to control the amplitude of the longitudinal movement (represented by arrow D1) of the insulating sleeve 22 relative to the lead body 20 by blocking the movement longitudinal (shown by arrow D1) of the insulating sleeve 22 beyond the stop element 40 (respectively below—depending on the position of the insulating sleeve 22 relative to the stop element 40).

According to the first embodiment, the abutment element 40 is a ring-shaped protrusion 42 which extends from the lead body 20 and around the lead body 20 and which therefore projects from the lead body 20. The stop element 40 is not limited to an annular geometry and can take a different form of protuberance as long as the stop element is dimensioned so as to block a longitudinal displacement of the insulating sleeve 22. In a variant, the lead body can comprise two stop elements which are positioned so that the insulating sleeve 22 is capable of being moved longitudinally between the two stop elements.

Figure 3:
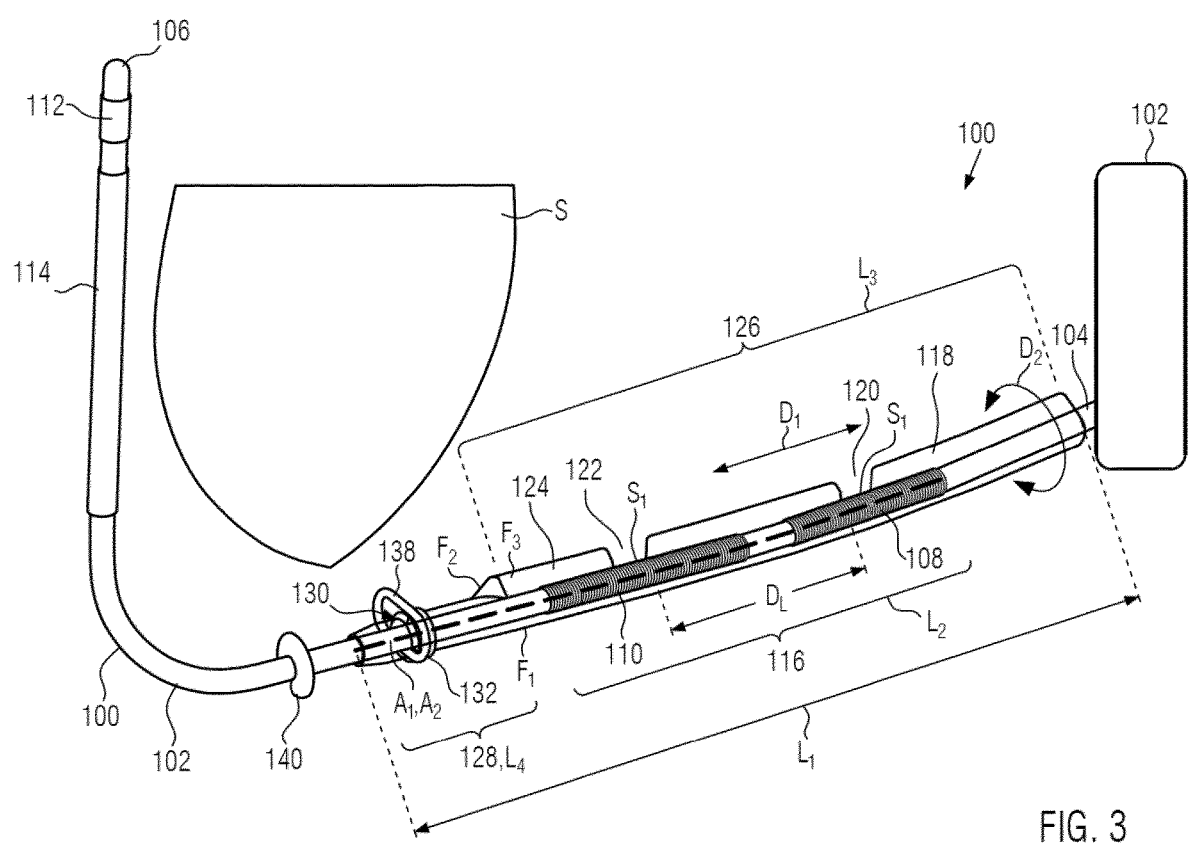
FIG. 3 represents a schematic and transparent view of a subcutaneous lead according to a second embodiment of the present invention.

FIG. 3 shows a schematic view and by transparency of a subcutaneous lead 100 according to a second embodiment of the present invention. In comparison with the first embodiment, the subcutaneous lead 100 of the second embodiment is connected to a housing 102 of a medical device of the defibrillator type, which is implanted subcutaneously (the sternum of a patient is indicated by the reference "S" in FIG. 3). The subcutaneous lead 100 of the second embodiment is thus configured for both a detection function and a defibrillation function.

The lead 100 has a lead body 102 delimited by two ends 104, 106; the end 104 being connected to the housing 102 (this is the proximal end of the lead 100) and the end 106 corresponding to the distal end of the lead 100.

According to the second embodiment, the lead 100 comprises a first sensing electrode 108, a second sensing electrode 110 and a third sensing electrode 112. The lead 100 also comprises a defibrillation electrode 114. According to the configuration of the second embodiment, the first sensing electrode 108 is placed proximally on the lead body 102 while the third sensing electrode 112 is placed at the distal end 106 of the lead body 102. The second sensing electrode 110 is placed between the first sensing electrode 108 and the third sensing electrode 112. The defibrillation electrode 114 is in turn placed between the second sensing electrode 108 and the third sensing electrode 112.

In the same method as the sensing electrode 16 of the first embodiment and its variants, the sensing electrodes 108, 110, 112 are formed from a single filament or from several filaments wound (s) around the body of lead 102.

The sensing electrodes 108, 110, 112 of the subcutaneous lead 100 allow the detection of surface electrical signals whose processing makes it possible to deduce therefrom the cardiac activity of a patient whereas the defibrillation electrode 114 has a defibrillation function. The practician thus needs to adjust the positioning of the lead 100 while ensuring both the optimal functioning of the detection function and of the defibrillation function. In order to adjust in particular the positioning of the dipole 116 formed by the first sensing electrode 108 and the second sensing electrode 110 to improve the quality of surface detection, the subcutaneous lead 100 of the present invention comprises an insulating sleeve 118 into which the lead body 102 is threaded and which at least partially covers the first sensing electrode 108 and the second sensing electrode 110.

As described with respect to the insulating sleeve 22 of the first embodiment, the insulating sleeve 118 according to the second embodiment is displaceable relative to the lead body 102. The insulating sleeve 118 is thus displaceable longitudinally (represented by the double arrow D1) and radially (represented by the double arrow D2) relative to a central axis A2 of the lead body 102. Respectively, the lead body 102 is movable longitudinally (represented by the double arrow D1) and radially (represented by the double arrow D2) with respect to a central axis A1 of the insulating sleeve 118.

In comparison with the insulating sleeve 22 of the first embodiment, the insulating sleeve 118 has a length L1 along a central axis A1 of the insulating sleeve 118 longer than a length L2 of the dipole 116 along one of central axis A2 of the lead body 102. In addition, the insulating sleeve 118 according to the second embodiment comprises two lateral openings 120, 122 in a side wall 124 of the insulating sleeve 118 so that a first lateral opening 120, such as a window is positioned above the first sensing electrode 108 and a second lateral opening 122, such as a window, is positioned above the second sensing electrode 110.

According to the second embodiment, the first lateral opening 120 and the second lateral opening 122 have an identical geometry. However, in a variant, the first and second lateral openings 120, 122 could be of different shape with respect to each other. The geometry of each lateral opening 120, 122 can thus vary and be specifically designed to adapt to the detection needs and/or the therapeutic needs of the patient.

Thus, the adjustment of the position of the insulating sleeve 118 makes it possible to fulfill the limitations induced by the fixed configuration, inter alia, of the sensing electrodes 108, 110 of the dipole 116 relative to the lead body 102. As a result, the insulating sleeve 118 allows a practician to have a subcutaneous lead 100 with a dipole 116 of sensing electrodes 108, 110 with variable geometry, thus making it possible to best adapt to the morphology of a patient and to be able to minimize the detection of surface muscle noise and therefore to avoid the detection of artifacts which could lead to the delivery of inappropriate shock, for example. Thus the distance of the dipole from the defibrillation electrode 114 and the third electrode 112 can be adjusted by the practician during implantation.

The first lateral opening 120 and the second lateral opening 122 of the insulating sleeve 118 thus make it possible to selectively expose at least partially a respective surface S1 of the first sensing electrode 108 and of the second sensing electrode 110, that is to say the surface S1 of each sensing electrode 108, 110 which is not covered by the insulating sleeve 118. The area of each exposed surface S1 can preferably be defined during the design of the insulating sleeve 118, as well as the longitudinal distance DL between the first lateral opening 120 and the second lateral opening 122 relative to a central axis A1 of the insulating sleeve 118. The determination of these geometry parameters (S1, DL) of the insulating sleeve 118 makes it possible to configure the dipole 116 formed by the first sensing electrode 108 and the second sensing electrode 110. This gives variable geometry to the subcutaneous lead 100, which makes it possible to improve the quality of the surface detection thanks to an adjusted positioning of the dipole 116. The practician can also, during the implantation of the lead 100, adapt the positioning of the lateral openings 120, 122 above the first and second sensing electrodes 108, 110 in order to optimize the positioning of the dipole 116, in particular with respect to the third distal sensing electrode 112.

In addition, as described in the first embodiment, the lateral openings 120, 122 of the insulating sleeve 118 make it possible to obtain sensing electrodes 108, 110 of sectoral type and not annular. The sectoral nature of the lateral openings 120, 122 of the insulating sleeve 118 make it possible in particular to preferentially orient the exposed surface S1 of the sensing electrodes 120, 122 towards the cardiac mass. The preferential orientation of the exposed surface S1 of the dipole 116, in particular towards the muscle mass of the implanted patient, makes it possible in particular to minimize the detection of surface muscle noise and therefore potentially to avoid the detection of artefacts which can lead to inappropriate shocks.

In addition, in the second embodiment, the adjustment of the orientation of an electric field created from the dipole 116 of the lead 100 towards a patient's heart mass can be used for a cardiac stimulation function; for example, in combination with a defibrillation function.

As in the first embodiment, the insulating sleeve 118 is formed in one piece which comprises along a central axis A1 a first portion 126 of length L3 and a second portion 128 of length L4. The first portion 126 of the insulating sleeve 118 has a substantially polygonal cross section, here triangular, while the second portion 128 of the insulating sleeve 118 has a substantially circular cross section.

The first portion 126 of the insulating sleeve 118 is thus provided with a side wall 124 along the central axis A1 of the insulating sleeve 118 which essentially comprises three flat faces F1, F2, F3.

In a variant, the first portion 126 of the insulating sleeve 118 does not necessarily have a triangular geometry section but comprises a side wall along a central axis A1 of the insulating sleeve 118 itself comprising at least one planar surface.

The flat faces F1, F2, F3 of the side wall 124 of the first portion 126 of the insulating sleeve 118 each provide a support surface for the insulating sleeve 118 with the muscle tissues of a patient. The flat faces F1, F2, F3 then make it possible to maintain, in particular by friction, the orientation of the insulating sleeve 118 relative to the lead body 102 in the body of a patient, by avoiding an involuntary movement in rotation (represented by the double arrow D2) of the insulating sleeve 118 around the lead body 102, during implantation and during the life of the implanted patient.

The second portion 108 of the insulating sleeve 118, the cross section of which is essentially circular, comprises in turn fixing means 130 allowing a practician to immobilize the insulating sleeve 118 to the lead body 102, and to attach the assembly insulating sleeve 118 and lead body 102 to the muscle tissue of a patient. As in the first embodiment of the invention, the fixing means 130 is provided by a groove 132 on the second portion 108 which is transverse to a central axis A1 of the insulating sleeve 118. The groove 136 is adapted to receive a wire ligature 138. Thus, once the positioning defined by the practician, according to the quality of the electrical signals detected for example, the insulating sleeve 118 and the lead body 102 are then secured to the chest of a patient by a conventional ligation technique, the ligature wire 138 encompassing both the insulating sleeve 118 and the lead body 102 at the groove 38, and the patient's muscle tissue.

The insulating sleeve 118 is thus fixed via the ligature wire 138 to the patient's muscle tissue, in the event of an involuntary movement of the lead 100 in the patient's body, this would have no impact on the configuration of the dipole 116 itself because the position and orientation of the exposed surfaces S1 of the dipole 116 are ensured by the fixing between the insulating sleeve 118 and the patient's muscle tissue (and therefore, to a certain extent, independently of the position of the lead 100). Especially since the insulating sleeve 118 can also comprise at least one stop element 140, as described in the first embodiment, arranged on the lead body 102 which allows the amplitude of the longitudinal displacement to be controlled (represented by arrow D1) of the insulating sleeve 118 relative to the lead body 102 by blocking the longitudinal movement (represented by arrow D1) of the insulating sleeve 118 beyond the stop element 140 (respectively below—depending on the position of the insulating sleeve 118 relative to the stop element 40).

The embodiments described are simply possible configurations and it should be borne in mind that the individual characteristics of the first embodiment and the second embodiment can be combined with one another or provided independently of each other.

The invention claimed is:

1. A subcutaneous lead for an implantable cardiac device, in particular for a defibrillator or/and a pacemaker comprising:
   a lead body comprising at least one sensing electrode; and
   an insulating sleeve into which the lead body is threaded,
   wherein the insulating sleeve is movable longitudinally and radially relative to a central axis of the lead body so as to at least partially cover the at least one sensing electrode with the insulating sleeve.

2. The subcutaneous lead of claim 1, wherein the insulating sleeve has a length along a central axis of the insulating sleeve longer than a length of the sensing electrode along a central axis of the sensing electrode; and wherein the insulating sleeve comprises a lateral opening in a side wall of the insulating sleeve so that the lateral opening is positioned above the sensing electrode.

3. The subcutaneous lead of claim 1, wherein the lead body further comprises a second sensing electrode; and wherein the insulating sleeve at least partially covers the first sensing electrode and the second sensing electrode.

4. The subcutaneous lead of claim 3, wherein the insulating sleeve comprises two lateral openings in a side wall of the insulating sleeve so that a first lateral opening is positioned above the first sensing electrode and a second lateral opening is positioned above the second sensing electrode.

5. The subcutaneous lead of claim 4, further comprising:
a third sensing electrode disposed distally on the lead body; and
a defibrillation electrode;
such that the defibrillation electrode is positioned between the third sensing electrode and an assembly formed by the first and second sensing electrodes;
the insulating sleeve at least partially covering the first sensing electrode and the second sensing electrode.

6. The subcutaneous lead of claim 3, wherein the assembly formed by the first and second sensing electrodes is configured for a cardiac stimulation function.

7. The subcutaneous lead of claim 1, wherein a first portion of the insulating sleeve along a central axis of the insulating sleeve comprises a side wall which itself comprises at least one flat surface, in particular a portion of the insulating sleeve along a central axis of the insulating sleeve, has a cross section relative to a central axis of the insulating sleeve of polygonal geometry.

8. The subcutaneous lead of claim 7, wherein a second portion of the insulating sleeve along a central axis of the insulating sleeve comprises at least one fixing means configured to prevent longitudinal movement of the insulating sleeve relative to a central axis of the lead body and/or for attaching the insulating sleeve to a muscular tissue.

9. The subcutaneous lead of claim 1, wherein the lead body comprises at least one stop element projecting from the lead body at least partially around the lead body capable of blocking a longitudinal movement of the insulating sleeve relative to the central axis of the lead body.

10. The subcutaneous lead of claim 3, wherein at least one of the first sensing electrode and the second sensing electrode is a flexible electrode comprising one or more filaments wound around the lead body.

11. The subcutaneous lead of claim 1, wherein the insulating sleeve is realized in at least two separate parts, each part of the insulating sleeve comprising at least one lateral opening.

12. The subcutaneous lead of claim 1, wherein the insulating sleeve comprises a radio opaque material.

* * * * *